US009248258B2

(12) United States Patent
Roman et al.

(10) Patent No.: US 9,248,258 B2
(45) Date of Patent: Feb. 2, 2016

(54) METHOD AND APPARATUS FOR SECURING I.V. NEEDLE AND LUER FITTING

(75) Inventors: Stephen B. Roman, Phoenix, AZ (US); Gary S. Kehoe, Glendale, AZ (US)

(73) Assignee: CareFusion 303, Inc., San Diego, CA (US)

(*) Notice: Subject to any disclaimer, the term of this patent is extended or adjusted under 35 U.S.C. 154(b) by 2627 days.

(21) Appl. No.: 11/316,076

(22) Filed: Dec. 22, 2005

(65) Prior Publication Data

US 2006/0211994 A1 Sep. 21, 2006

Related U.S. Application Data

(60) Provisional application No. 60/662,419, filed on Mar. 16, 2005.

(51) Int. Cl.
*A61M 5/32* (2006.01)
*A61M 25/02* (2006.01)

(52) U.S. Cl.
CPC ........ *A61M 25/02* (2013.01); *A61M 2025/0246* (2013.01); *A61M 2025/0266* (2013.01)

(58) Field of Classification Search
CPC ..................... A61M 25/02; A61M 2025/0206; A61M 2025/0246; A61M 2025/028; A61M 2025/0266
USPC .......... 604/93.01, 164.04, 174, 179, 180, 351
See application file for complete search history.

(56) References Cited

U.S. PATENT DOCUMENTS

| | | | |
|---|---|---|---|
| 3,900,026 A * | 8/1975 | Wagner .......................... | 128/888 |
| 4,534,762 A * | 8/1985 | Heyer ........................... | 604/180 |
| 4,633,863 A * | 1/1987 | Filips et al. .................... | 128/846 |
| 4,669,458 A | 6/1987 | Abraham et al. ............. | 128/133 |
| 4,737,143 A | 4/1988 | Russell | |
| D302,041 S | 7/1989 | Gentelia et al. ................ | D24/52 |
| D305,363 S | 1/1990 | Gentelia et al. ................ | D24/52 |
| 5,116,324 A | 5/1992 | Brierley et al. | |
| 5,776,106 A * | 7/1998 | Matyas ......................... | 604/180 |
| 6,124,521 A | 9/2000 | Roberts | |
| 6,689,104 B2 | 2/2004 | Bierman | |
| RE38,597 E | 9/2004 | Lane, Jr. | |
| 6,827,707 B2 | 12/2004 | Wright et al. | |
| 6,837,875 B1 | 1/2005 | Bierman | |
| D503,977 S | 4/2005 | Bierman | |

OTHER PUBLICATIONS

2005 Conmed Patient Care Products Catalog, cover page and pp. A.53-A.57.
Conmed Corporation webpage for Veni-Gard® SP—Special Port I.V. Dressing System (visited Jun. 22, 2005).
(Continued)

*Primary Examiner* — Christopher D Koharski
*Assistant Examiner* — Elizabeth K So
(74) *Attorney, Agent, or Firm* — McDermott Will & Emery LLP (57) ABSTRACT

An IV holder for securing an IV needle and Luer fitting assembly. The IV holder includes a frame defining an aperture with a first portion and a second portion, the first portion of the aperture further being covered by a transparent window for protecting and securing the IV needle insertion site. The second portion of the aperture is disposed to fit a cylindrical Luer fitting. The holder is adhesively applied to a patient's skin and situated so that the needle insertion site is under the window and the first portion of the aperture while the Luer fitting is disposed within the second portion of the aperture.

8 Claims, 6 Drawing Sheets

(56) References Cited

OTHER PUBLICATIONS

Conmed Corporation webpage for Veni-Gard® AP—All Purpose I.V. Dressing System (visited Jun. 22, 2005).
Conmed Corporation webpage for Veni-Gard® ML—Jugular Line/Central Line I.V. Dressing System (visited Jun. 22, 2005).
Conmed Corporation webpage for Veni-Gard® TM—Universal I.V. Dressing System (visited Jun. 22, 2005).
Conmed Corporation webpage for Veni-Gard® TM Jr.—Small Limb I.V. Dressing System (visited Jun. 22, 2005).
Conmed Corporation webpage for Veni-Gard® TPN—Central Line/Ports/TPN I.V. Dressing System (visited Jun. 22, 2005).
Conmed Corporation webpage for ClearSite® TM Transparent Membrane Dressing/IV Securement (visited Jun. 22, 2005).

* cited by examiner

METHOD AND APPARATUS FOR SECURING I.V. NEEDLE AND LUER FITTING

This application claims priority from U.S. provisional application Ser. No. 60/662,419, filed on Mar. 16, 2005, the disclosure of which is hereby incorporated by reference in its entirety.

TECHNICAL FIELD OF THE INVENTION

The present invention relates generally to securement devices for stabilizing venous access devices such as intravenous needles and their associated Luer fittings to a patient's skin.

BACKGROUND OF THE INVENTION

Intravenous (IV) needles are frequently used in medical procedures. As with any invasive procedure, IV-related infections are a significant concern. Where repeated access to the bloodstream is needed, IV catheters are used. These catheters frequently use cylindrical Luer fittings and valves as an alternative to traditional needle based injection ports. However, in order to be effective, catheters must avoid dislodgment as well as avoid bloodstream infection and local site infection.

IV catheter securement poses a number of challenges. In order to maximize residence time, IV catheters must be secured from dislodgement or causing damage from unwanted movement. The insertion site should also be easily inspected for and protected from contamination or infection. Preferably, the catheter port can also be readily serviced.

Traditional methods call for securing the catheter insertion site with a gauze dressing or a transparent film with adhesive tape. Adhesive tape is problematic in that it is difficult to keep sterile and is prone to irritate a patient's skin. The use of a transparent film is preferable since it serves as a pathogenic barrier and permits viewing of the insertion site. However, transparent films are problematic in that the film eventually loosens from casual contact and permits catheter migration.

The disparity in diameter between an IV needle and a Luer fitting further complicates the securement problem. While an adhesive strip can be taped over the Luer fitting to secure the Luer fitting to the skin, the opaque tape prevents visual inspection of the Luer fitting. Moreover, securing the Luer fitting under a transparent film or under adhesive tape is problematic in that the larger diameter of the Luer fitting acts as a spacer and creates a gap between the film or tape and the patient's skin. This gap defeats the infection barrier purpose of securement.

Another approach is embodied by an IV holder produced by ConMed, Inc., of Utica, N.Y., generally described in U.S. Pat. No. 4,669,458. The ConMed, Inc., device is a catheter dressing with a generally tear-drop shaped frame with a base strip that completely encloses a polymer window. In operation, the polymer window is positioned over the area where the intravenous needle enters the skin and the body of a patient. The transparent cylindrical Luer fitting used to secure the intravenous needle to a tubing assembly itself is adhesively secured taping down the base strip over Luer fitting.

One significant disadvantage of the ConMed dressing is that because the Luer fitting is secured by and under the base strip, it is not readily inspected for blockage. In addition, it is also difficult to disconnect or replace the Luer fitting without removing the entire dressing. Yet another disadvantage is that owing to the comparative larger diameter of the Luer fitting as compared to the intravenous needle and intravenous tubing, securing the Luer fitting with the dressing tends to create gaps between the elevated dressing and the patient's skin. This gap is detrimental to a primary function of the IV holder, i.e. to seal the area around the intravenous needle to prevent fluid and foreign contaminants from entering the patient's body at the insertion site.

There is thus a need for a IV holder to alleviate the disadvantages of those IV holders available in the present art. Specifically, the IV holder of the present invention readily permits access to the Luer fitting and maintains a closer seal around the needle insertion site.

SUMMARY OF THE INVENTION

The present invention is related to IV holders. The holder comprises of a frame made of a contoured or flexible material that is capable of being secured to a patient's skin. The frame further defines an aperture with a first portion and a second portion. A transparent window is secured to the first portion of the aperture while the second portion of the aperture is left open. The holder is used to secure an IV insertion site by positioning the insertion site under the window in the first portion of the aperture and the larger diameter Luer fitting in the open second portion of the aperture.

In a preferred embodiment, the holder is composed of a soft pliable material forming a frame. The frame surrounds an aperture with a first portion and a second portion. A flexible transparent film is secured to the frame over the first portion of the aperture to form a protective barrier over the first portion of the aperture. Preferably, at least a portion of the underside of the frame has an adhesive to facilitate securement of the IV holder on a patient's skin.

When placing the IV holder, the holder is positioned so that the film covered first portion of the aperture is over the IV needle insertion site. The holder is further oriented so that the Luer fitting upstream from the IV needle insertion site is placed in the second portion of the aperture.

The second portion of the frame is perforated for removal. This permits access to and servicing of the Luer fitting without removing the holder. Additional adhesive strips are provided with the IV holder for securing the Luer fitting or the IV apparatus upstream of the insertion site. These strips may also have a writable surface so that patient identification or other information can be written thereon.

The components of the IV holder can also be made of more rigid materials and contoured to fit around a patient's body by using a hard plastic for a frame and a clear plastic window with more rigidity. To ensure the best possible fit, the outer surface of the Luer fitting can include raised surfaces or depressions matching their complements on the Luer fitting to lock the cover onto the Luer fitting for additional stability. The matching IV holder and Luer fitting can be provided in kit form.

DETAILED DESCRIPTION OF THE PREFERRED EMBODIMENTS

Figure 1:
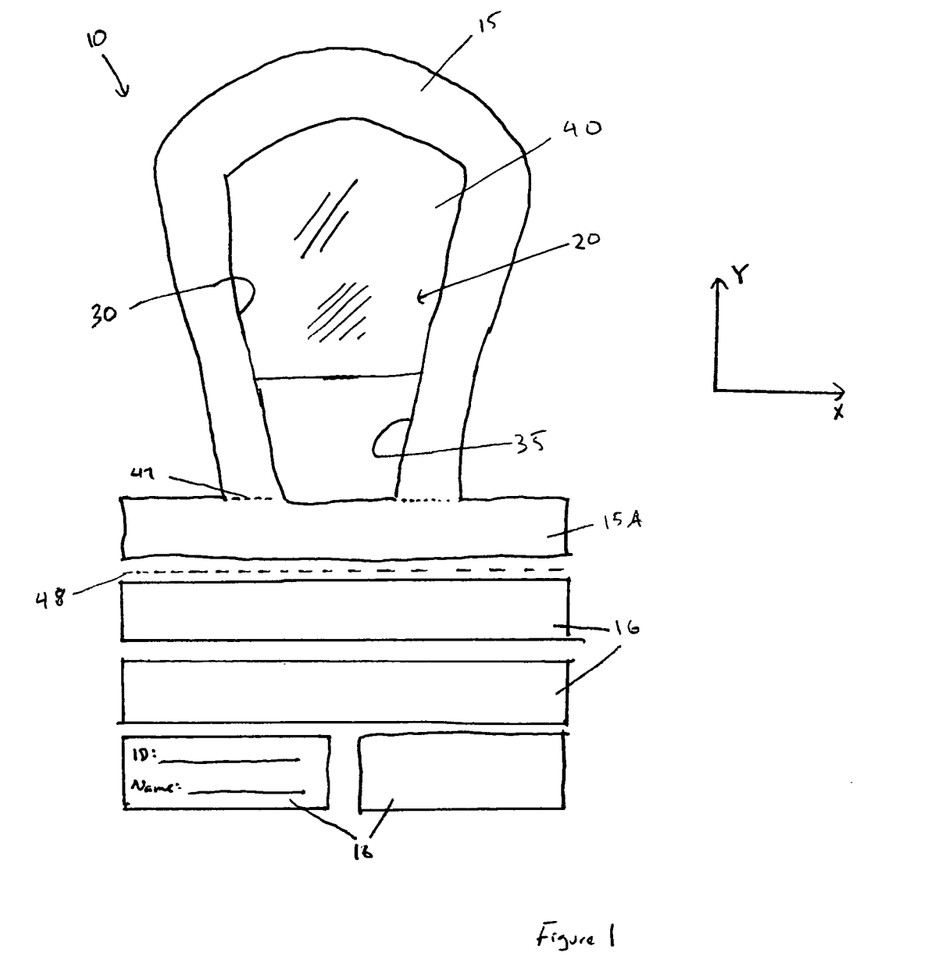
FIG. 1 illustrates a preferred embodiment of the IV holder of the invention.
Figure 2:
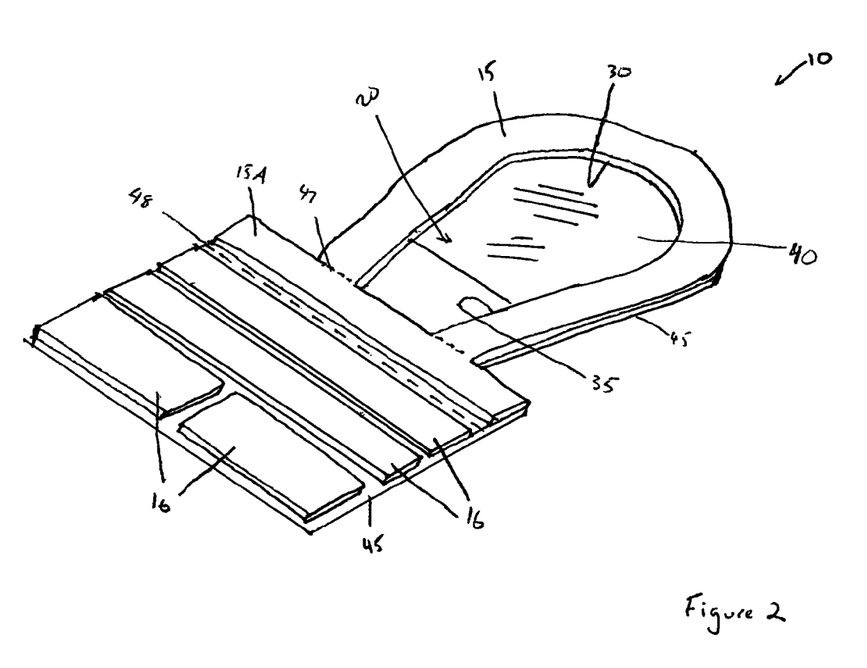
FIG. 2 is a perspective view of the IV holder of FIG. 1.
Figure 3:
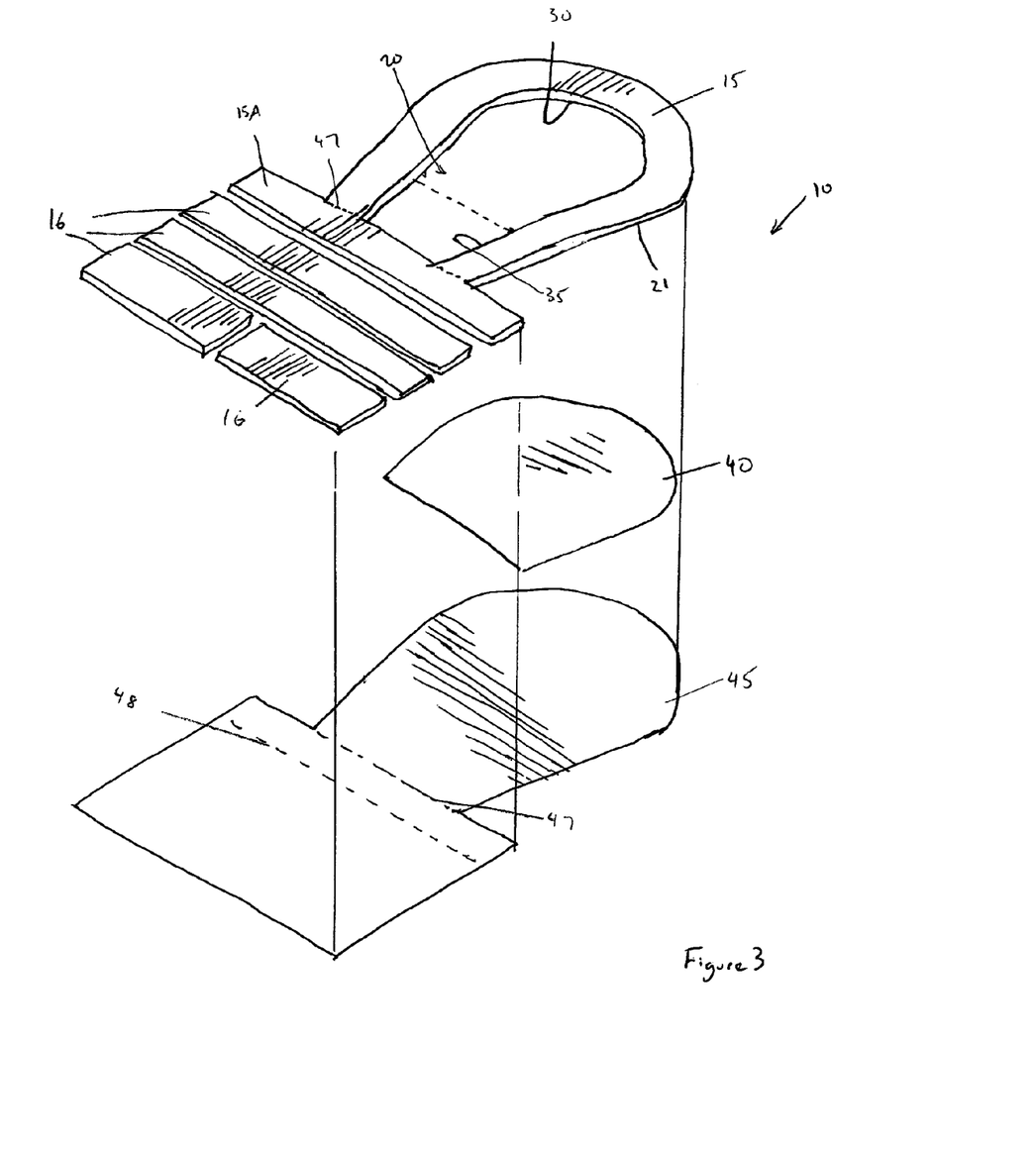
FIG. 3 is an exploded view of the IV holder of FIG. 1.

Referring now to the drawings, FIGS. 1-3 show a preferred embodiment of the IV holder of the present invention. The IV holder 10 includes frame 15 and base strip 15A and further includes additional strips. The frame 15 and base strip 15A define an aperture 20 with a first portion 30 and a second portion 35. The area of first portion 30 should be large enough to surround an IV needle insertion site. While the first portion 30 of the aperture 20 is shown to be larger than the second portion 35, this is not necessary so long as the second portion 35 is large enough to accommodate the length of a Luer fitting.

While a horseshoe shape is depicted, frame 15 can be of any shape such as circular, rectangular or other polygonal shapes. Curved shapes are more preferred, however, because they are more resistant to dislodging the adhesive seal than hard edges and corners.

The bottom surface 21 of frame 15, base strip 15A, and strips 16 are coated with an adhesive that facilitates the securement of the IV holder 10 to the skin of a patient. The frame 15 is preferably made of a soft pliable material with an adhesive back such as the 1/16 inch polyethylene foam tape 1772 manufactured by 3M®. Additional strips 16 may be fabricated from similar materials. It should also be understood that the frame 15 can be made of a more rigid material such as a hard plastic to resist removal and increase durability.

The adhesive underside of frame 15, base strip 15A, and strips 16 are releasably secured to backing 45 until they are needed. A frangible portion, such as a perforation 47, permit base strip 15A and its adhesive backing to be detached from frame 15. Likewise, lines of weakening or perforation 48 permit separation of strips 16 from frame 15 and base strip 15A or from each other for separate application or to reservation for later use. Backing 45 can contain frangible portions to permit removal of the backing 45 from frame 15 by the operator with one hand.

Figure 4:
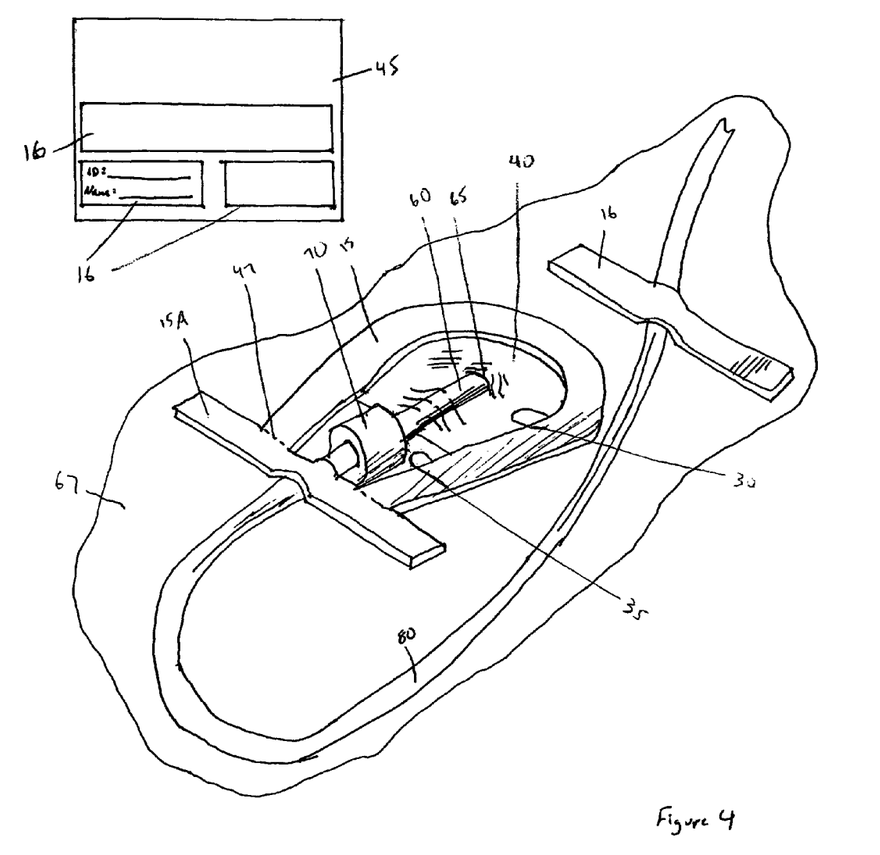
FIG. 4 is a perspective view showing the IV holder of FIG. 1 in operation with an IV needle, Luer fitting, and tubing.

The additional strips 16 provided can be used for a number of purposes. While the IV holder is initially secured by frame 15 and base strip 15A, base strip 15A is removable for servicing the Luer fitting. When servicing is complete, the Luer fitting can be resecured by using the strip 16 in place of the removed base strip 15A. Strips 16 are also used to secure the IV tubing upstream of the insertion site as shown in FIG. 4. The surface of strip 16 may further include a writable surface for the notation of patient identification or other information.

A window 40 covers the first portion 30 of the aperture 20. The peripheral edge of the window 40 is permanently secured to frame 15. Window 40 preferably is made of a urethane or similar material and is flexible, clear, breathable and sterilizable to minimize contamination when the IV holder is applied. The underside of window 40 optionally includes an adhesive coating to secure an IV needle (not shown) to the skin and minimize gaps between the window 40 and the skin to further minimize contamination. With these qualities, window 40 is positioned over and provides a viewable window to the insertion site so that any contamination can be monitored while simultaneously providing a barrier around the insertion site.

While not strictly necessary, there is a benefit to be obtained if the IV holder 10 is longer (i.e. in the Y direction) than it is wide (i.e. in the X direction). A narrower width provides for better support and securement of the holder 10. Additionally, a longer length allows for added versatility in the positioning of the holder relative to the Luer fitting.

FIG. 4 depicts the IV holder 10 in operation. Backing 45 is torn along lines of weakening 48 to separate pieces 15 and 15A from pieces 16. An IV needle 60 is inserted into the body of a patient at insertion site 65 through the skin 67. The needle 60 is connected to Luer fitting 70, to which the IV tubing 80 is connected. Backing 45 is removed from holder pieces 15 and 15A to expose the adhesive on the holder 10. The holder 10 is then pressed against the skin 67 of the patient to cover the exposed portions of needle 60. Window 40 is positioned over the insertion site 65 and is further positioned so that Luer fitting 70 is in the open second portion 35 of the aperture 20. In this position, insertion site 65 can be visually inspected through the window 40 and the window 40 is contoured around the needle 65 so as to be substantially in close proximity or contact with the patient's skin 67.

The holder 10 is further preferably positioned so that cylindrical Luer fitting 70 is positioned in the second portion 35 of the aperture 20. This permits the Luer fitting to extend upwardly through the second portion 35 of the aperture 20 and does not interfere with window 40. Base strip 15A is used to secure the IV tubing 80 to the patient's skin upstream of the Luer fitting 70. Further adhesive strips 16 are be used to secure the IV tubing 80 at other positions to minimize the risk of dislodging the IV assembly.

Secured in this manner, the window 40 of IV holder 10 provides a barrier against infection and contamination of and a way to visually inspect the insertion site 65. Because the window 40 secures the IV needle 60, which has a small diameter in comparison to Luer fitting 70, the flexible window 40 substantially contours around the diameter of the needle 60 and establishes a seal by minimizing gaps between the window 40 and the patient's skin 67. Luer fitting 70 is secured in part by base strip 15A upstream and the holder 10 and window 40 downstream. By positioning the Luer fitting 70 in the second portion 35 of aperture 20, the excessive height and diameter of fitting 70 (in comparison to needle 60 and tubing 80) does not interfere with the securement of the IV holder 10.

In the event that it is necessary to detach the Luer fitting 70 for service or to clear needle 60, base strip 15A is readily removed by tearing along lines of weakening 47. Luer fitting 70 is then unthreaded from needle 60, serviced, and replaced without the need to remove or otherwise disturb frame 15 and window 40 of the IV holder 10. Once the service is complete, the Luer fitting 70 and the IV tubing 80 is secured by one of the reserved adhesive strips 16.

Figure 5:
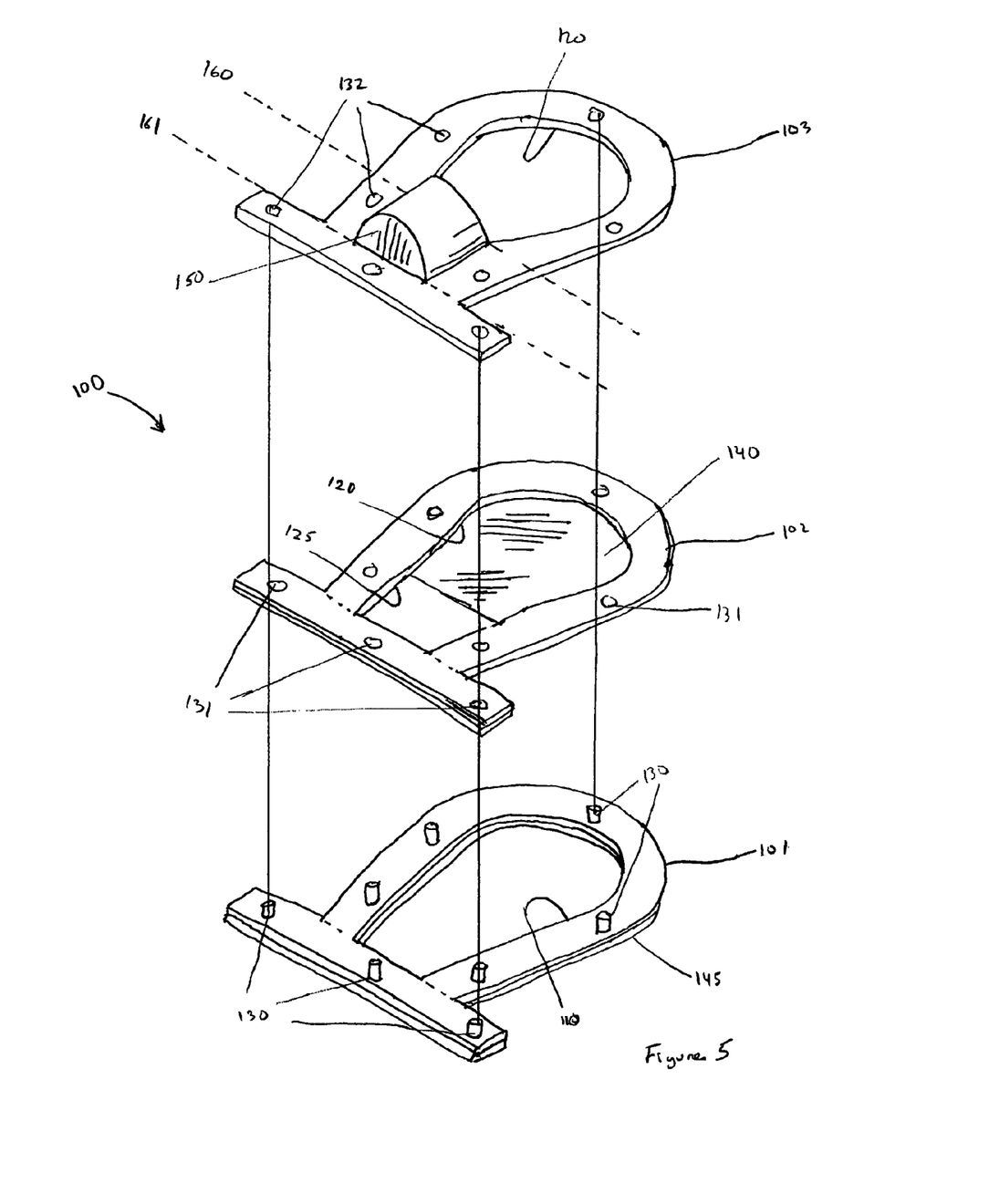
FIG. 5 is an exploded view of an alternate embodiment of the IV holder of the present invention.

FIG. 5 shows an shows an alternate preferred embodiment of the IV holder 100 of the present invention. The IV holder comprises of a base frame 101, a spacer frame 102, and a cover plate 103. Base frame 101 defines an aperture 110 and also includes a plurality of upstanding pins 130. The underside of base frame 101 is coated with a peelable adhesive backing 145.

Spacer frame 102 defines an aperture 110 which can be divided into a first portion 120 and a second portion 125. A transparent flexible window 140 is secured to the spacer frame 102 over first portion 120 of aperture 110. Spacer frame 102 further includes apertures 131 formed therethrough frame 102 corresponding to pins 130 on the base frame 101.

Cover plate 103 defines the first portion 120 of aperture 110 and further includes apertures 132 formed therethrough corresponding to pins 130 on the base frame 100. The cover plate 103 also includes a transparent semi-cylindrical housing 150 dimensioned and shaped to seat over a cylindrical Luer fitting positioned in the second portion 125 of aperture 110. Housing 150 is preferably rigid for added protection and securement of the Luer fitting underneath. A rigid housing also minimizes the risk of dislodging or displacing the IV holder or IV needle by the patient's actions. The housing 150 may also include other covers or members shaped to cover portions of an IV needle or fittings.

In use, the base frame 101 is adhesively secured to the patient's skin afer the insertion of the IV needle. Spacer frame 102 and cover plate 103 are then mounted on base frame 101 by matching pins 130 with apertures 131 and 132. Ideally, the base frame 101 is positioned so that the IV needle is in the first portion 120 of aperture 110 and the Luer fitting is in second portion 125 of aperture 110 aperture 125 and under the housing 150 of cover plate 103.

While base frame 101, spacer frame 102 and cover plate 103 are shown to be generally coextensive with each other in FIG. 5, it should be recognized that this need not be the case. For example, the cover plate 103 can be limited to the material between dashed lines 160 and 161. Moreover, the spacer frame 102 and cover plate 103 can be integrated into a single unit.

Housing 150 is be preferably designed to be universally applied to and used with most if not all Luer fittings in the marketplace. Alternatively, housing 150 can be designed so that its interior has a raised surface complementing a similar surface on a matching Luer fitting 170.

Figure 6:
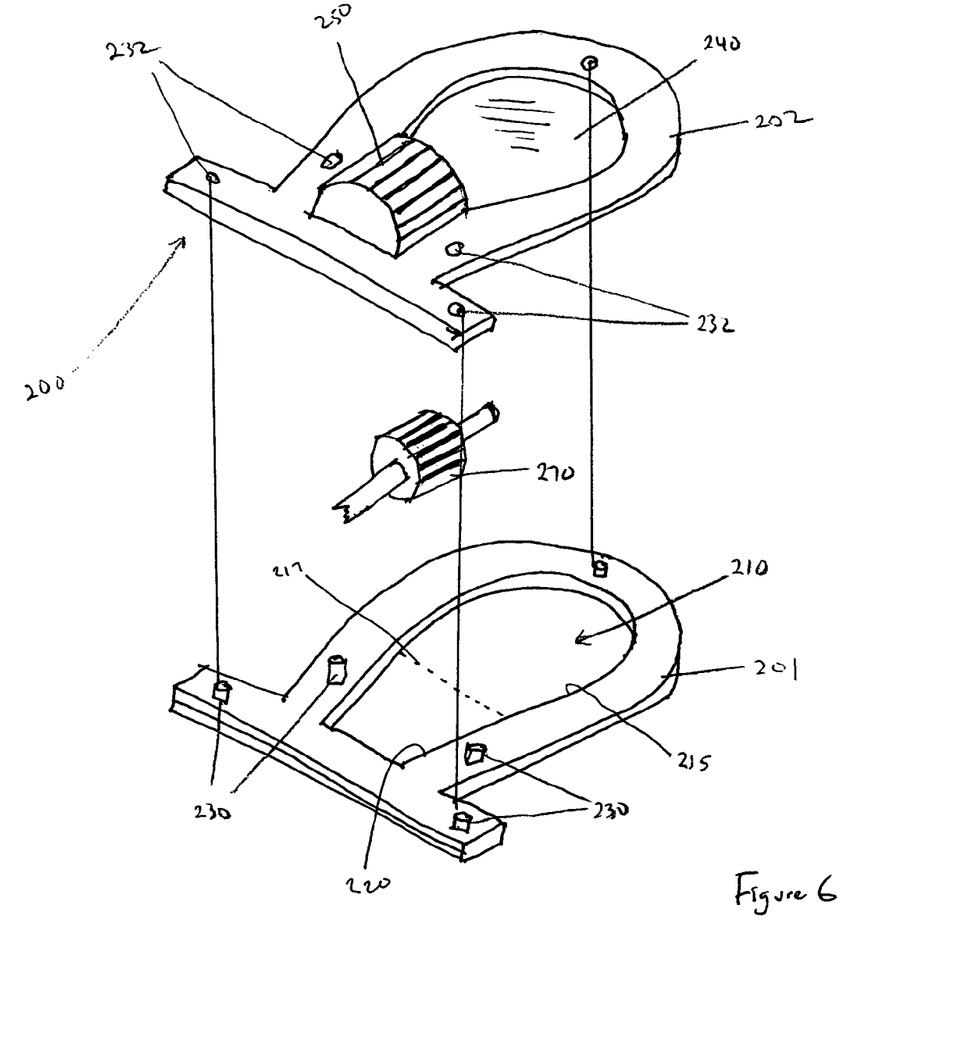
FIG. 6 is an exploded view of another embodiment of the present invention.

FIG. 6 shows a kit with an IV holder and an accompanying Luer fitting. The IV holder 200 comprises a base plate 201 which is adhesively secured to the patient's skin, the base plate forming an aperture 210 and having upstanding pins 230 around its perimeter. The aperture 210 can be divided into a first portion 215 and a second portion 220, shown by the dashed line 217. Cover plate 202 fits on top of base plate 201 and is secured by apertures 232 corresponding to upstanding pins 230. Cover plate 202 further has a window 240 positioned over the first portion 215 of aperture 210 to cover the needle insertion site and a transparent housing 250 positioned over the second portion 220 of aperture 210 for securing a Luer fitting 270. The outer surface of Luer fitting 270 is shown with a pattern of grooves complementing a pattern of grooves on the inside of housing 250 such that when the housing 250 is positioned over Luer fitting 270, they are securely mated.

In lieu of grooves, the complementary surfaces of the interior of housing 250 and the outer surface of Luer fitting 270 can be designed using ridges, tabs, or other uneven surfaces. In addition to providing an additional level of securement between the Luer fitting and the IV holder, such a design promotes the use of matching sizes of IV holders and Luer fittings.

While the various descriptions of the present invention are described above, it should be understood that various features can be used singly or in combination thereof. Therefore, this invention is not to be limited to the specific preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly set forth in the appended claims.

What is claimed is:

1. A holder for securing an intravenous (IV) needle, a Luer fitting, and an attached IV tube to a patient comprising:
   a frame with a top surface, a bottom surface and an outer perimeter defining an aperture with a first portion and a second portion;
   at least a portion of the bottom surface of the frame having an adhesive adapted to secure the frame to the skin; and
   a substantially transparent viewing window secured to the frame over the first portion of the aperture and not over the second portion of the aperture, where the second portion of the aperture is open and configured to receive the Luer fitting with a gap between the Luer fitting and the holder.

2. The holder of claim 1 wherein a side of the frame adjacent to the second portion of the aperture is detachable.

3. The holder of claim 1 wherein a side of the frame adjacent to the second portion of the aperture is configured to secure the attached IV tube to the patient.

4. The holder of claim 1 wherein at least part of the frame is curved.

5. The holder of claim 1 wherein the frame comprises of a flexible material.

6. The holder of claim 1 wherein the frame is rigid.

7. A kit including the holder of claim 1 wherein the kit further includes at least one adhesive tab.

8. The kit of claim 1 wherein at least one adhesive tab comprises a writable surface.

* * * * *